(12) United States Patent
Jagiella et al.

(10) Patent No.: US 8,981,795 B2
(45) Date of Patent: Mar. 17, 2015

(54) MEASURING ARRANGEMENT FOR DETERMINING ELECTRICAL CONDUCTIVITY OF A MEASURED LIQUID

(75) Inventors: Manfred Jagiella, Nürtingen-Reudern (DE); Marco Völker, Döbeln (DE)

(73) Assignee: Endress + Hauser Conducta Geselllschaft fur Mess-Und Regeltechnik mbH + Co. KG, Gerlingen (DE)

( * ) Notice: Subject to any disclaimer, the term of this patent is extended or adjusted under 35 U.S.C. 154(b) by 573 days.

(21) Appl. No.: 13/349,719

(22) Filed: Jan. 13, 2012

(65) Prior Publication Data
US 2012/0182027 A1 Jul. 19, 2012

(51) Int. Cl.
*G01R 27/28* (2006.01)
*G01R 27/04* (2006.01)
*G01R 27/08* (2006.01)
*G01N 27/06* (2006.01)
*G01N 27/02* (2006.01)
*G01R 27/22* (2006.01)

(52) U.S. Cl.
CPC .............. *G01N 27/06* (2013.01); *G01N 27/025* (2013.01); *G01N 27/023* (2013.01); *G01R 27/22* (2013.01)
USPC ............ 324/654; 324/634; 324/693; 324/713

(58) Field of Classification Search
CPC ... G01N 27/023; G01N 27/025; G01N 27/06; G01R 27/22
USPC .................................. 324/654, 634, 693, 713
See application file for complete search history.

(56) References Cited

U.S. PATENT DOCUMENTS

| 3,806,798 A | 4/1974 | Gross |
| 7,479,864 B2 * | 1/2009 | Weller et al. .................. 336/200 |
| 7,696,762 B2 * | 4/2010 | Quackenbush et al. ........ 324/696 |
| 2008/0218302 A1 | 9/2008 | Volker et al. |

FOREIGN PATENT DOCUMENTS

| DE | 19611174 C1 | 7/1997 |
| DE | 10026052 A1 | 6/2001 |
| DE | 102006018623 A1 | 10/2007 |
| DE | 102006025194 A1 | 12/2007 |

OTHER PUBLICATIONS

German Language Search Report dated Jul. 27, 2011.

* cited by examiner

*Primary Examiner* — Amy He
(74) *Attorney, Agent, or Firm* — Bacon & Thomas, PLLC

(57) ABSTRACT

A measuring arrangement for determining electrical conductivity of a measured liquid, comprising: a container, in which the measured liquid is accommodated, a gradiometer arrangement, comprising an exciter coil, a first receiving coil and a second receiving coil, wherein the first and the second receiving coils are arranged symmetrically relative to the exciter coil, and a measurement circuit embodied to excite the exciter coil for producing an alternating magnetic field passing through the first receiving coil, the second receiving coil and the measured liquid. The receiving coils are influenced in different manner by the magnetic field induced by the alternating magnetic field in the measured liquid and directed counter to the alternating magnetic field. The measurement circuit is furthermore embodied to register an electrical signal of the receiving coils and to derive from such the electrical conductivity of the liquid.

12 Claims, 3 Drawing Sheets

MEASURING ARRANGEMENT FOR DETERMINING ELECTRICAL CONDUCTIVITY OF A MEASURED LIQUID

TECHNICAL FIELD

The invention relates to a measuring arrangement for determining electrical conductivity of a measured liquid.

BACKGROUND DISCUSSION

In process measurements technology, or in industrial measurements technology, for measuring the conductivity of a liquid, frequently conductivity sensors are used, which work according to an inductive or a conductive measuring principle.

Known from EP 990 894 B1, for example, is a conductive conductivity sensor, which has at least two electrodes, which, for measuring, are immersed in a measured medium. For determining the electrical conductivity of the measured medium, the resistance or conductance of the electrode measuring path in the measured medium is determined. In the case of a known cell constant, the conductivity of the measured medium can be ascertained therefrom. For measuring the conductivity of a measured liquid by means of a conductive conductivity sensor, it is absolutely required to bring at least two electrodes in contact with the measured liquid.

Inductive conductivity sensors comprise a transmitting coil and a receiving coil, which are, as a rule, embodied as toroidal coils, and which surround a traversing opening chargeable with the measured liquid, so that, upon exciting the transmitting coil, a closed electrical current path can form extending within the medium. The path passes through the transmitting coil and the receiving coil. By evaluating the electrical current- or voltage signal of the receiving coil in response to the signal of the transmitting coil, consequently, the conductivity of the measured liquid can be ascertained. Examples of inductive conductivity sensors are known, for example, from DE 197 47 273 B4, EP 999 441 B1 or DE 4116468 A1. These conductivity sensors are embodied as probes, which, for measuring conductivity, are immersed into the measured liquid, so that measured liquid flows around the two toroidal coils.

Pharmaceutical, chemical, biological, biochemical or biotech processes are performed, in increasing measure, in single-use, process containers (also referred to as 'disposables', or, in the biotech field, for instance, 'disposable bioreactors'). Such single-use, process containers can be, for example, flexible containers, e.g. bags, tubes or fermenters, respectively, bioreactors. Bioreactors, or fermenters, possess, frequently, feed- and drain lines, which can be embodied, for example, as tubes. In the feed- and drain lines, also fixed tubular pieces can be applied. After terminating a process the single-use, process container can be disposed of. In this way, complex cleaning- and sterilization methods can be avoided. Especially, through the use of single-use, containers, the risk of cross contamination is avoided and, therewith, bio- and process safety increased. Single-use, process containers are, as a rule, made of synthetic material, for instance, plastic.

The processes running in the single-use, process containers are sealed relative to the environment. Before introducing process media into the single-use, process containers, such must, as a rule, be sterilized. For this purpose in biochemical, biological, biotechnological and pharmaceutical applications, frequently, gamma radiation is used. Also, during the running of a process in a single-use fermenter or single-use reactor, the penetration of germs from the environment into the interior of the container must be avoided, in order not to degrade or corrupt the process.

In order to monitor the processes, it can be necessary to measure physical or chemical, measured variables of the media contained in the container. Measured variables to be monitored can include, besides electrical conductivity, for example, temperature, pH-value, cell density, optical transmission or concentration of a chemical substance, for example, a certain kind of ion or a certain element or a certain compound. For assuring and maintaining sterility within the process container, it is especially desirable, to measure these measured variables with contactless methods.

Known from DE 37 18 111 C2 is an arrangement for contactless, inductive measuring of the conductivity of a measured liquid, in the case of which the measured liquid flows through a line, for example, a hose or a pipe, which has two liquid paths, so that a liquid loop is formed. A first, toroidal coil serving as exciter coil surrounds the first liquid path of the liquid loop, a second, toroidal coil serving as receiving coil surrounds the second liquid path of the liquid loop, so that, upon exciting of the exciter coil, a closed electrical current path forms within the measured liquid flowing in the liquid loop. The path passes through the exciter coil and the receiving coil, so that an electrical current, or a voltage, is induced in the receiving coil, based on which the conductivity of the measured liquid can be ascertained.

Known from DE 198 23 836 C2 is another arrangement for contactless, inductive measuring of the conductivity of a measured liquid, which is supposed to be suitable for application in the case of single-use, process containers. This arrangement has only a single toroidal coil, which surrounds a pipeline flowed through by the measured liquid. The toroidal coil can be excited to produce a time variable, magnetic field, which induces an electrical current within the liquid flowing through the line. In contrast to the arrangement described in DE 37 18 111 C2, however, no electrical current induced in the liquid is measured, but, instead the power loss of the measuring arrangement brought about by the electrical current flow in the liquid and the ohmic resistance of the liquid and therefrom the conductivity of the measured liquid is ascertained.

Both the arrangement described in DE 37 18 111 C2 as well as also the arrangement known from DE 198 23 836 C2 are, indeed, suitable for contactless measurement. However, they can only be applied in connection with a tubular line carrying the measured liquid and extending axially through the toroidal coils. The arrangement according to DE 37 18 111 C2 even requires a line embodied in special manner to form a liquid loop, in order to have a closed electrical current path through the measured liquid. They are, consequently, for example, suitable only for measuring conductivity in specially dimensioned lines. Thus, they can not be applied directly, for example, in the bag fermenters installed, frequently, in single-use, process technology, but, instead only in a suitably dimensioned supply or drain line.

Another apparatus for contactless measurement of electrical conductivity in a measured liquid is known from DE 199 48 465 A1. The apparatus is based on the principle of known eddy current methods, as they are applied, for example, in materials testing. The apparatus has a cylindrical exciter coil for producing a magnetic, alternating field in the measured liquid, a cylindrical receiving coil arranged within the windings of the cylindrical exciter coil for measuring a magnetic field resulting from the alternating magnetic field and the magnetic field of electrical currents, which are induced in the liquid due to the alternating magnetic field and whose magnetic field is directed counter to the alternating magnetic field, and a corresponding measurement circuit for ascertaining the conductivity of the liquid from the measured resulting magnetic field. This apparatus can be arranged outside of a container of any geometry, and measure contactlessly through a non electrically conductive wall of the container the conductivity of a contained measured liquid therein. Since not only the magnetic field induced in the measured liquid, but also the magnetic field of the exciter coil acts on the receiving coil, the electrical signal of the receiving coil will always be relatively large. Especially, the part of the magnetic field from the exciter coil predominates significantly compared to the part of the electrical signal of the receiving coil due to the conductivity of the measured liquid. This degrades the accuracy of measurement of the apparatus, especially in the case of small conductivities of the measured liquid.

SUMMARY OF THE INVENTION

An object of the invention is to overcome the disadvantages of the state of the art. Especially, an apparatus and a method for measuring the conductivity of a measured liquid should be provided, which is suitable for applications in process measurements technology, especially in chemical, pharmaceutical, biological or biotechnological processes, which are performed in single-use, process containers. This requires especially the assuring of sterile conditions within the process container and an as simple as possible, and therewith, cost effective, embodiment of the apparatus for measuring conductivity, wherein, however, a high accuracy of measurement in a broad measuring range should be available.

This object is achieved by a measuring arrangement for determining electrical conductivity of a measured liquid, comprising: a container, in which the measured liquid is accommodated, a gradiometer arrangement, comprising an exciter coil, a first receiving coil and a second receiving coil, wherein the first and the second receiving coils are arranged symmetrically relative to the exciter coil, and a measurement circuit embodied to excite the exciter coil for producing an alternating magnetic field passing through the first receiving coil, the second receiving coil and the measured liquid, wherein the receiving coils are exposed in different measure to a magnetic field induced by the alternating magnetic field in the measured liquid and directed counter to the alternating magnetic field, wherein the measurement circuit is furthermore embodied to register an electrical signal of the receiving coils and to derive from such the electrical conductivity of the liquid.

Such a gradiometer system and the associated measurement circuit can be simply constructed and, thus, be suitable for a single-use application in combination with a single-use, process container. Especially, with the measuring arrangement of the invention, a contactless measuring can occur, so that sterility within the container is assured. If the measuring occurs contactlessly, the same gradiometer arrangement can optionally also be applied multiply in combination with different single-use, process containers.

The first and the second receiving coils are preferably equally embodied, especially they have equal geometry, equal number of windings and the same line cross section of the electrical conductors forming the windings. The receiving coils are exposed in different measure to the magnetic field induced in the measured liquid and directed counter to the alternating magnetic field. For example, can the receiving coils can be permeated differently strongly by the magnetic field, so that an electrical current or a corresponding voltage induced in the first receiving coil by the magnetic field, differs from the electrical current, or the corresponding voltage induced in the second receiving coil by the magnetic field. This is the case, for example, when a magnetic field gradient forms across the receiving coils. Especially, an option is to embody and/or to arrange the receiving coils such that one of the receiving coils does not receive the magnetic field induced in the measured liquid, so that in this receiving coil no measurable electrical current, or no measurable voltage is induced by the magnetic field induced in the measured liquid. The other receiving coil can receive the magnetic field induced in the measured liquid, so that this magnetic field produces a measurable contribution to the electrical current induced in the receiving coil.

The container can especially be embodied as a single-use, process container. Such single-use, process containers are, frequently, formed of an electrically insulating material, especially a synthetic material, e.g. plastic. The exciter coil, the first receiving coil and the second receiving coil can be arranged outside of the container. In order to assure that the receiving coils are exposed in different measure to a magnetic field induced in the measured liquid by the alternating magnetic field and directed counter to the alternating magnetic field, or that, in measurement operation, a magnetic field gradient forms across the receiving coils and these are therewith influenced by the magnetic field in different manner, the first and the second exciter coils can be arranged at different distances from a wall of the container and therewith at different distances frin the measured liquid.

The exciter coil and the first and the second receiving coils can in a first embodiment be embodied as cylindrical coils, wherein the winding advance of the coil windings extends in the direction of the cylinder axis of the respective cylindrical coils, and be applied on a rod, especially a cylindrical rod, of an electrically insulating material, in such a manner that the cylinder axes of the exciter coil and the first and second receiving coils coincide with one another and the rod axis, and wherein the first and the second receiving coils are arranged at equal distances to the exciter coil on oppositely lying sides of the exciter coil.

The exciter coil and the first and the second receiving coils can in a second embodiment be formed by conductive traces on an electrically insulating substrate, especially a circuit board or a ceramic substrate, having at least two plan parallel surfaces. The electrically insulating substrate can be, for example, a circuit card of a circuit card material, for example, an organic material, wherein, advantageously, the organic material is phenolic resin+paper (FR1, FR2), epoxide resin+paper (FR3), epoxide resin+glass fiber weave (FR4, FR5), polyimide and/or polyester. The substrate can also be of an electrically non conductive ceramic, an LTCC-ceramic (Low Temperature Cofired Ceramic) or an Al2O3-ceramic. The exciter coil and the first and the second receiving coils can be formed by conductive traces of copper, silver, palladium, gold, aluminum or combinations thereof.

The electrically not conducting substrate can have one or more plies. The exciter coil can be arranged, for example, on a first area of the substrate, while the receiving coils are arranged on a second area of the substrate essentially parallel to the first area. In the case of a single ply substrate, for example, a single ply circuit card, the first area can be formed by the front side of the circuit card and the second area by the rear side of the circuit card. In the case of a multi-ply substrate, for example, a multi-ply circuit card, the first area can be the surface of a first ply and the second area the surface of an additional ply. In an advantageous further development, in the case of application of a multi-ply substrate, electrical contacting of the coils, which serve for connection to the measurement circuit, can extend in another ply of the substrate than the coil windings. Thus, the gradiometer arrangement can be constructed especially compactly.

The conductive traces forming the exciter coil and the receiving coils can be, for example, a single coil winding. They can be also a number of coil windings, especially spirally shaped windings, extending in a plane. Preferably, the gradiometer arrangement arranged on the substrate has a central, gradiometer axis extending through the coil center of the exciter coil perpendicular to the substrate surface, and, respectively, to the substrate plies. The two receiving coils have the same distance from the exciter coil, measured parallel to the gradiometer axis. The coil centers of the two planar receiving coils have, moreover, in each case, the same distance from the gradiometer axis.

The substrate with the exciter coil, the first receiving coil and the second receiving coil can be arranged outside of the container in the region of a container wall in such a manner that the first receiving coil has a smaller distance to the container wall than the second receiving coil. In this way, it is assured that the measured liquid accommodated in the container likewise has a smaller distance to the first receiving coil than to the second receiving coil, so that the magnetic field induced in the measured liquid by the alternating magnetic field of the exciter coil acts in lesser measure on the second receiving coil than on the first receiving coil.

The measurement circuit can be arranged at least partially on the same substrate as the exciter coil and the receiving coil. This permits an especially compact sensor construction. For contacting the measurement circuit arranged on the substrate, the circuit card can have a plug contact. Via this plug contact, the measurement circuit can be connected with a superordinated unit, for example, an electronic data processing installation, especially a measurement transmitter, which supplied the circuit arranged on the substrate with energy and receives measurement signals of the measurement circuit arranged on the substrate.

Alternatively, the first and the second receiving coils can be arranged within the container. This arrangement is especially advantageous when the container is single-use fermenter with a flexible container wall. For example, in this case, the first and second receiving coils can be embodied as planar substrate coils formed by a conductive trace on a circuit card, while the exciter coil can be embodied as a planar formed coil by a conductive trace on the rear side of the circuit card substrate. The circuit card substrate can be integrated in a wall of the single-use fermenter, e.g. by sealedly fitting it in a seat provided in the wall or connecting it permanently, e.g. by a welded connection, with the wall, wherein the substrate-side carrying the receiving coils faces toward the container interior. The sterilization of the container with the integrated gradiometer arrangement can then occur by means of gamma radiation. After use of the single-use container, such can be disposed of, together with the substrate. For this, the embodiment of the gradiometer arrangement with planar coils arranged on a circuit card substrate is especially well suited, since the material costs of such an embodiment are small, and the embodiment is also inexpensive to manufacture.

When the receiving coils are arranged within the container, a different permeation of the two receiving coils by the magnetic field induced in the measured liquid, or a magnetic field gradient across the receiving coils, can be assured by having the first receiving coil be wetted directly by the measured liquid, while the second receiving coil is isolated from the measured liquid by an electrically insulating coating.

The first receiving coil and the second receiving coil are preferably embodied in such a manner that the alternating magnetic field produced in the first receiving coil by the electrical current, or the corresponding voltage, induced by the exciter coil is phase shifted by 180° relative to the electrical current, or relative to the corresponding voltage, induced in the second receiving coil by the alternating magnetic field.

In an option for an embodiment, the phase shift by 180° is assured by connecting the first receiving coil and the second receiving coil in series, wherein the first receiving coil has a winding handedness opposite to the second receiving coil. The electrical current, and, respectively, the voltage induced in the receiving coils by the direct interaction with the alternating magnetic field of the exciter coil have, because of the symmetric arrangement of the receiving coils relative to the exciter coil, the same magnitude, however, in each case, opposite sign. Thus, the measurement circuit registers from the two exciter coils connected in series the signal zero. If a conductive measured liquid is located in the vicinity of the gradiometer arrangement, eddy currents brought about by the alternating magnetic field of the exciter coil are produced therein. If the receiving coils are arranged in such a manner that they are exposed in different measure to the magnetic field of the eddy currents, e.g. in that the first receiving coil has a smaller distance to the measured liquid than the second receiving coil, one of the receiving coils, in the example, the first receiving coil, is more strongly permeated by the magnetic field of the eddy currents than the other. In other words, there forms across the receiving coils, dependent on the conductivity of the measured liquid, a magnetic field gradient, which is detected by means of the receiving coils. Since the magnetic field of the eddy currents in the measured liquid opposes the alternating magnetic field caused by the exciter coil, in the receiving coil exposed more strongly to the magnetic field of the eddy currents, thus in the example, the first receiving coil, a lesser electrical current, or a smaller voltage, is induced than in the other receiving coil. The measurement circuit is embodied to output the difference signal between the first receiving coil and the second receiving coil as the measurement signal. Advantageous in such a difference circuit is that the measurement signal is not dependent on the basic signal produced by the direct coupling of the magnetic field of the exciter coil with the receiving coils. Thus, also small measurement signals can be safely registered with sufficient accuracy.

A method for measuring electrical conductivity of a measured liquid in a single-use, process container, includes steps as follows:

Arranging a gradiometer arrangement having an exciter coil, a first receiving coil and a second receiving coil, which are arranged symmetrically relative to the exciter coil, in the region of a wall of the single-use, process container or integrated in a wall of the single-use, process container;

exciting the exciter coil for producing an alternating magnetic field, which passes through the first receiving coil and the second receiving coil and induces in the measured liquid a magnetic field directed counter to the alternating magnetic field, wherein the receiving coils are exposed in different measure to the magnetic field induced in the measured liquid by the alternating magnetic field and directed counter to the alternating magnetic field;

registering an electrical signal of the receiving coils, especially a difference of a first electrical signal induced in the first receiving coil and an electrical signal induced in the second receiving coil, and ascertaining the electrical conductivity of the measured liquid based on the electrical signal registered by the receiving coils.

BRIEF DESCRIPTION OF THE DRAWINGS

The invention will now be explained in greater detail based on the examples of embodiments illustrated in the drawing, the figures of which show as follows:

FIG. 3 b) a schematic representation of the rear view of the planar gradiometer arrangement of FIG. 2;

DETAILED DISCUSSION IN CONJUNCTION WITH THE DRAWINGS

Figure 1:
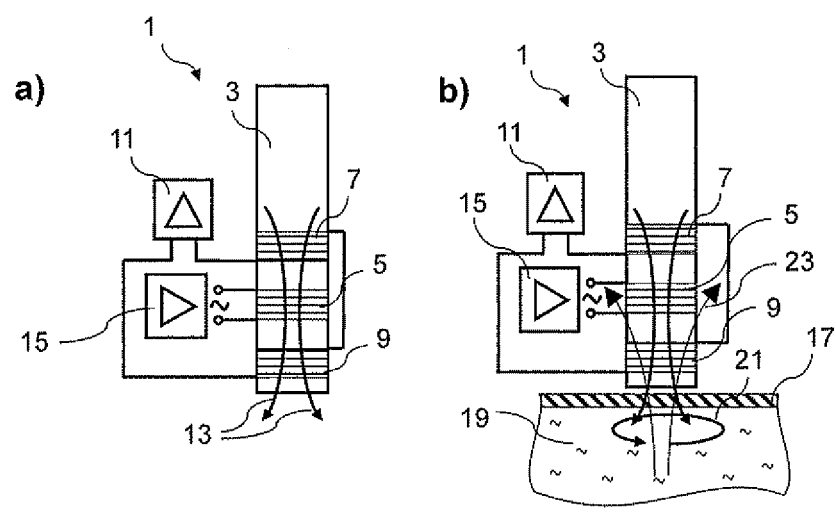
FIG. 1 is a schematic representation of a gradiometer arrangement of a measuring arrangement for measuring conductivity of a measured liquid according to a first example of an embodiment.

FIGS. 1 a) and b) show a schematic representation of a gradiometer arrangement 1, including an exciter coil 5, a first receiving coil 7 and a second receiving coil 9. The exciter coil 5, the first receiving coil 7 and the second receiving coil 9 are embodied as cylindrical coils, which are wound on cylindrical rod 3 of electrically non conductive material, e.g. of an electrically non conductive, synthetic material, such as a plastic, or an electrically non conductive ceramic. The windings of the coils extend on the cylindrical lateral surface of the rod 3 and their winding advance extends parallel to the cylinder axis of the rod 3. The three coils are arranged axially one after the other, wherein the exciter coil 5 is positioned centrally between the two receiving coils 7, 9.

The exciter coil 5 is connected with a driver stage 15, which is embodied to supply the exciter coil with an alternating voltage. The alternating magnetic field 13 of the exciter coil 5 passes through the first receiving coil 7 and the second receiving coil 9 in equal measure, since the receiving coils 7, 9 have, in each case, the same distance from the exciter coil 5, and, thus, are arranged symmetrically relative to the exciter coil 5. The alternating magnetic field 13 induces, consequently, in both receiving coils 7, 9 electrical currents that are equal in magnitude. In the example illustrated here, the first receiving coil 7 and the second receiving coil 9 have different winding handedness on and are connected in series. The receiver stage 11 outputs, consequently, a difference signal formed from the difference of the electrical currents induced in the receiving coils, or, depending on the circuit, formed from the voltages induced in the receiving coils. This difference signal has in the case of FIG. 1 a), in which no electrically conductive medium is present in the vicinity of the gradiometer arrangement 1, the value zero.

In the case of FIG. 1 b), the gradiometer arrangement 1 is arranged in the vicinity of an electrically non conductive, container wall 17 of a single-use, process container, in which a measured liquid 19 serving as process medium is accommodated, wherein, in the example shown here, the rod 3 is oriented perpendicular to the container wall 17. Due to the alternating magnetic field 13, there are produced in the measured liquid 19, as a function of its electrical conductivity, eddy currents 21, whose magnetic field 23 is directed counter to the alternating magnetic field 13. The second receiving coil 9 arranged nearer to the container wall and, therewith, to the measured liquid 19 is exposed in greater measure to the magnetic field 23 of the eddy currents 21, i.e. it is more strongly passed through by its field lines, than the more remote, first receiving coil 7. Therewith, there results a magnetic field gradient between the first and the second receiving coils. Correspondingly, there is induced in the second receiving coil 9 an electrical current of different magnitude, here larger, than in the first receiving coil 7. The difference signal registered and output by the receiver stage 11 is therefore different from zero and directly proportional to the conductivity of the measured liquid 19. It can serve, consequently, as measure for the conductivity of the measured liquid 19.

Figure 2:
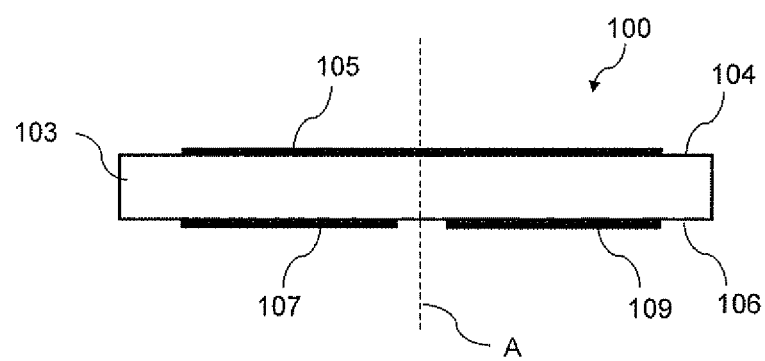
FIG. 2 is a schematic representation in side view of a planar gradiometer arrangement of a measuring arrangement for measuring conductivity of a measured liquid according to a second example of an embodiment.
Figure 3:
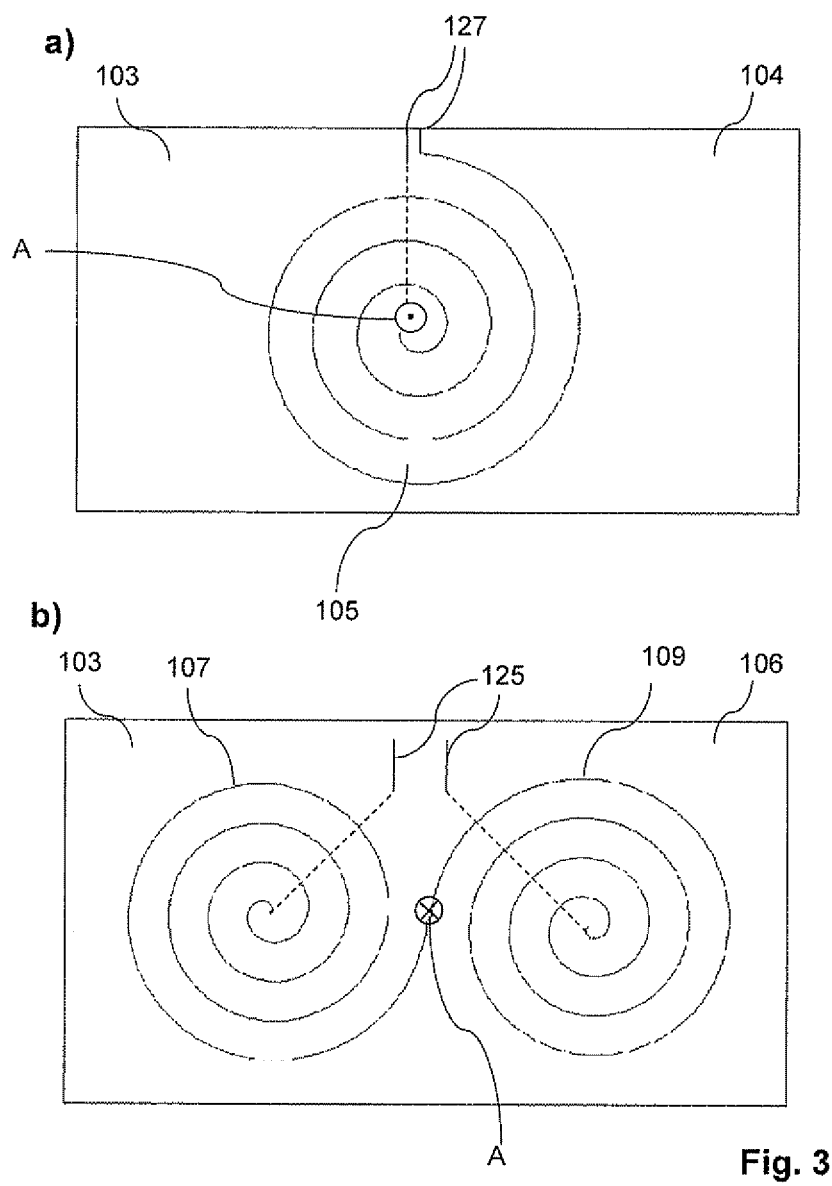
FIG. 3 a) is a schematic representation of the front view of the planar gradiometer arrangement of FIG. 2.

FIGS. 2 and 3 a) and b) show a schematic representation of a gradiometer arrangement 100 as a further example of an embodiment. FIG. 2 shows the arrangement in cross section, FIG. 3 a) shows the rear side and FIG. 3 b) the front view of the gradiometer arrangement 100. The gradiometer arrangement 100 includes an electrically insulating substrate 103, on which the exciter coil 105, the first receiving coil 107 and the second receiving coil 109 are applied in the form of conductive traces, especially metal conductive traces. In the present example, the substrate 103 is a multi-ply circuit card of a synthetic material, e.g. FR4, FR5. The coils have, in each case, spiral shaped conductive traces extending on a surface of the circuit card. The conductive traces form the coil windings, wherein the windings of the exciter coil 105 are arranged on the rear side 104 and the windings of the receiving coils 107, 109 on the front side 106 the circuit card. The two receiving coils 107, 109 have equal turns number- and length as well as the same diameter of the conductive traces forming the windings. The electrical contacting of the receiving coils 107, 109 and the exciter coil 105 occurs via conductive traces 125, 127, which extend at least partially on inner plies (then shown as dashed lines) of the circuit card.

Extending from the coil center of the exciter coil 105 perpendicularly to the circuit card plane is the gradiometer axis A. The coil centers of the receiving coils 107, 109 have the same distance from the gradiometer axis A. Since the front- and rear side 104, 106 the circuit card extend parallel to one another, the receiving coils 107, 109 have also the same distance from the exciter coil 105, measured parallel to the gradiometer axis A. Therewith, the receiving coils 107, 109 are arranged symmetrically in such a manner relative to the exciter coil 105 that an alternating magnetic field produced by applying an alternating voltage to the connections 127 of the exciter coil 105 pass through the two receiving coils 107, 109 in equal measure, and so induce an electrical current of equal magnitude in the two receiving coils 107, 109. The two receiving coils 107, 109 have opposite winding handedness and are connected in series, so that, at the connections 125, a difference signal of the induced electrical currents in the two receiving coils 107, 109 is registered. To the extent that neither of the two receiving coils 107, 109 is influenced by a supplemental magnetic field of a measured liquid or other electrically conductive object present in the vicinity of the receiving coils 107, 109, the difference signal on the connections 125 has the value zero.

The measurement circuit of the gradiometer arrangement 100 according to FIGS. 2 and 3 can be embodied analogously to the measurement circuit described for FIG. 1 with a driver stage 15 and a receiver stage 11.

Figure 4:
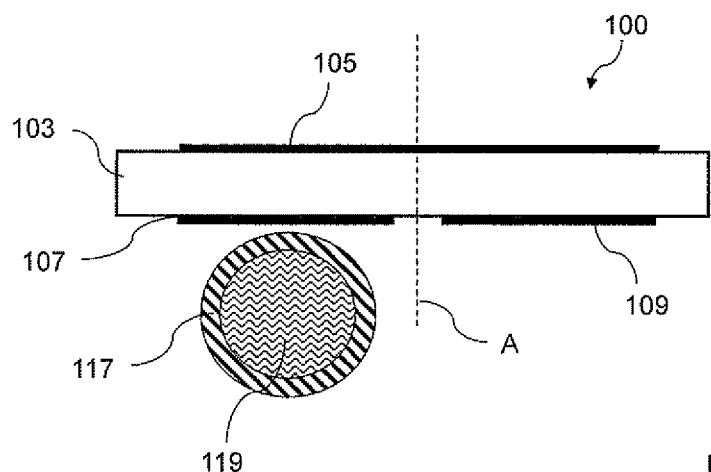
FIG. 4 is a schematic representation of a gradiometer arrangement integrated into the wall of a single-use, process container according to a third example of an embodiment.

FIG. 4 shows schematically a possible measuring arrangement for measuring electrical conductivity of a measured liquid 119 accommodated in a single-use, process container 117 with the gradiometer arrangement 100 illustrated in FIGS. 2 and 3. The single-use, process container 117 is embodied in this example as a line with a container wall of electrically non conductive, synthetic material. The gradiometer arrangement 100 is arranged in such a manner relative to the process container 117 that the first receiving coil 107 has a smaller distance to the container wall, and therewith also to the measured liquid, than the second receiving coil 119. As explained in detail based on the example of an embodiment shown in FIG. 1, a magnetic field formed by eddy currents in the measured liquid 119 upon the exciting of the exciter coil 105 and directed counter to the magnetic field of the exciter coil 105 influences the two receiving coils 107, 109 in different manner, so that, on the connections 125, a difference signal different from zero can be tapped. This is output from the receiver stage of the measurement circuit as measurement signal e.g. to a superordinated data processing system (not shown) connected with the measurement circuit, which derives from the measurement signal the electrical conductivity of the measured liquid and outputs such as measured value.

Figure 5:
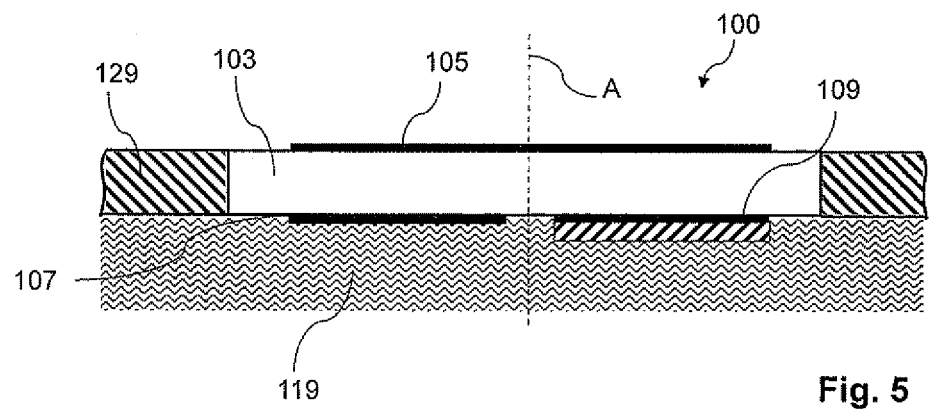
FIG. 5 is a schematic representation of a measuring arrangement for measuring conductivity of a measured liquid in a process container.

FIG. 5 shows, schematically, another example of a measuring arrangement for measuring, with the gradiometer arrangement 100 illustrated in FIGS. 2 and 3, electrical conductivity of a measured liquid 119 accommodated in a single-use, process container.

In this example of an embodiment, the substrate 103 is integrated into the wall 129 of the process container. If the substrate 103 is embodied as a synthetic material, circuit card, it can, for example, be mounted in a seat provided therefor in the container wall 129 or, as shown here, adhered or welded fixedly directly integrated into the container wall 129. The process container can be, for example, a single-use, reactor or fermenter with a flexible container wall 129. The process container can be sterilized with the gradiometer arrangement 100 integrated into the container wall 129 by means of gamma radiation before the introduction the measured liquid 119. The measurement circuit is, advantageously, arranged on the substrate 103 on its rear side facing away from the container interior or isolated from the substrate 103 outside of the container.

The substrate 103 is arranged in the container wall 129 in such a manner that the exciter coil 105 is located outside of the process container, while the two receiving coils 107 and 109 are arranged within the process container. The registering of conductivity measured values occurs, in manner equal to the example described with respect to FIG. 4, by exciting the exciter coil 105 for producing an alternating magnetic field, which passes through the receiving coils and induces in the measured liquid 119 a magnetic field directed counter to the alternating magnetic field. In order to prevent that the two receiving coils 107, 109 are permeated in equal manner by the magnetic field induced in the measured liquid 119, the second receiving coil 109 is provided with an insulating coating 131. In this way, a magnetic field gradient arises between the first and the second receiving coils 107, 109, so that, at the connections 125, a difference signal different from zero is registerable, which is directly proportional to the electrical conductivity of the measured liquid.

The invention claimed is:

1. A measuring arrangement for determining the electrical conductivity of a measured liquid, comprising:
   a container, in which the measured liquid is accommodated;
   a gradiometer arrangement, comprising an exciter coil, a first receiving coil and a second receiving coil, wherein said first receiving coil and said second receiving coils are arranged symmetrically relative to said exciter coil, and
   a measurement circuit embodied to excite said exciter coil for producing an alternating magnetic field passing through said first receiving coil, said second receiving coil and the measured liquid, wherein:
   said receiving coils are exposed in different measure to a magnetic field induced by said alternating magnetic field in the measured liquid and directed counter to the alternating magnetic field; and
   said measurement circuit is furthermore embodied to register an electrical signal of said receiving coils and to derive from such the electrical conductivity of the measured liquid.

2. The measuring arrangement as claimed in claim 1, wherein:
   the container is formed of an electrically insulating material and said gradiometer arrangement is arranged outside of the container.

3. The measuring arrangement as claimed in claim 1, wherein:
   said exciter coil and said first and said second receiving coils are embodied as cylindrical coils, and are applied on a rod of an electrically insulating material in such a manner that the cylinder axes of said exciter coil and said first and second receiving coils coincide with one another and with the rod axis; and
   said first and said second receiving coils are arranged at the same distance from said exciter coil on oppositely lying sides of said exciter coil.

4. The measuring arrangement as claimed in claim 1, wherein:
   said exciter coil and said first and said second receiving coils are formed by conductive traces on an electrically insulating substrate, especially a circuit card or a ceramic substrate.

5. The measuring arrangement as claimed in claim 4, wherein:
   said exciter coil is arranged on a first area of said substrate, and said receiving coils are arranged on a second area of said substrate essentially parallel to the first area.

6. The measuring arrangement as claimed in claim 4, wherein:
   said measurement circuit is arranged at least partially on the same substrate as said exciter coil and said receiving coils.

7. The measuring arrangement as claimed in claim 4, wherein:
   said substrate with said exciter coil, said first receiving coil and said second receiving coil is arranged outside of the container in such a manner that the container has a smaller distance to said first receiving coil than to said second receiving coil.

8. The measuring arrangement as claimed in claim 1, wherein:
   said first and said second receiving coils are arranged within the container.

9. The measuring arrangement as claimed in claim 8, wherein:
   said first receiving coil is wetted directly by the measured liquid, and said second receiving coil is isolated from the measured liquid by an insulating coating.

10. The measuring arrangement as claimed in claim 1, wherein:
said first receiving coil and said second receiving coil are embodied in such a manner that the electrical current, or the corresponding voltage, induced in said first receiving coil by the alternating magnetic field is phase shifted by 180° relative to the electrical current, or the corresponding voltage, induced in said second receiving coil by the alternating magnetic field.

11. The measuring arrangement as claimed in claim 10, wherein:
said first receiving coil and said second receiving coil are connected in series; and
said first receiving coil has a winding handedness opposite to that of said second receiving coil.

12. A method for measuring electrical conductivity of a measured liquid in a single-use, process container, comprising steps of:
arranging a gradiometer arrangement having an exciter coil, a first receiving coil and a second receiving coil, which are arranged symmetrically relative to the exciter coil, in the region of a wall of the single-use, process container or integrated in a wall of the single-use, process container;
exciting the exciter coil for producing an alternating magnetic field, which passes through the first receiving coil and the second receiving coil, especially symmetrically, and induced in the measured liquid a magnetic field directed counter to the alternating magnetic field, wherein the receiving coils are exposed in different measure to the magnetic field induced by the alternating magnetic field in the measured liquid and directed counter the alternating magnetic field;
registering an electrical signal of the receiving coils, especially a difference of a first electrical signal induced in the first receiving coil and an electrical signal induced in the second receiving coil; and
ascertaining the electrical conductivity of the measured liquid based on the registered electrical signal of the receiving coils.

* * * * *